United States Patent [19]

Alvarez

[11] 4,421,743

[45] * Dec. 20, 1983

[54] ANTIHYPERTENSION TREATMENT

[75] Inventor: Jose A. A. Alvarez, Carpatos, Mexico

[73] Assignee: T & R Chemicals, Inc., Clint, Tex.

[ * ] Notice: The portion of the term of this patent subsequent to Apr. 27, 1999 has been disclaimed.

[21] Appl. No.: 337,177

[22] Filed: Jan. 5, 1982

Related U.S. Application Data

[63] Continuation-in-part of Ser. No. 75,423, Sep. 14, 1979, Pat. No. 4,327,083, which is a continuation-in-part of Ser. No. 859,705, Dec. 12, 1977, abandoned.

[51] Int. Cl.³ ............................................. A61K 33/04
[52] U.S. Cl. .................................... 424/162; 424/154
[58] Field of Search .............. 424/180, 162, 333, 335, 424/267, 315, 325, 248.5, 154

[56] References Cited

U.S. PATENT DOCUMENTS 4,327,083  4/1982  Alvarez .............................. 424/162

Primary Examiner—Sam Rosen
Attorney, Agent, or Firm—Cushman, Darby & Cushman

[57] ABSTRACT

The treatment of mammals with alkali metals, alkaline earth metals and ammonium salts of sulfites and bisulfites suffering from hypertension is described.

4 Claims, No Drawings

ANTIHYPERTENSION TREATMENT

RELATED APPLICATIONS

This application is a continuation-in-part of my copending U.S. Ser. No. 75,423, filed Sept. 14, 1979, now U.S. Pat. No. 4,327,083, which in turn is a continuation-in-part of my copending application U.S. Ser. No. 859,705, filed Dec. 12, 1977, but now abandoned, the disclosure and contents of each of which applications are entirely incorporated herein by reference.

BACKGROUND OF THE INVENTION

Sodium bisulfite (usually shown by formula to be $NaHSO_3$) has heretofore been used for many commercial purposes, such as a preservative for prevention of the deterioration of liquid systems, such as food stuffs and of pharmaceutical solids, and has also been used medically both externally, such as for treatment of parasitic skin diseases, and internally such as for a gastrointestinal antiseptic. So far as now known, sodium bisulfite has never previously beeen used by man for the treatment of hypertension.

The solid sodium bisulfite of commerce reportedly consists chiefly of sodium metabisulfite, $Na_2S_2O_5$, and sodium bisulfite, and, for purposes of this invention, such is believed to possess the same properties as (and to be equivalent to) sodium bisulfite when dissolved in aqueous solution.

BRIEF SUMMARY OF THE INVENTION

There has now been discovered a class of inorganic agents, the members of which when introduced by ingestion, injection, absorption, or otherwise into a mammal (including man), produce avoidance, amelioration and/or improvement of a hypertensive condition in mammals and man when used in an antihypertensively effective amount as taught herein.

The active antihypertensive agents of the present invention are inorganic salts of sulfurous acid which display antihypertensive activity. Thus, these agents are selected from compounds in the group consisting of alkali metal, alkaline earth metal, and ammonium salts of sulfites and bisulfites (including metabisulfites) and mixtures thereof. Alkali metal particularly sodium and potassium bisulfites are presently preferred active agents, and, of these, sodium bisulfite is a presently most preferred active agent. Also, because of similar toxicological considerations, the calcium, magnesium, and ammonium compounds are also preferred.

In one aspect, the present invention is directed to the use of certain inorganic bisulfite and sulfite compounds as antihypertensive agents in human medicine.

In another aspect, the present invention is directed to a method for control of, and/or prevention of, hypertension in man by oral ingestion and/or injection of a pharmacologically effective amount of sodium bisulfite and/or other compound(s) within the scope of active agents of this invention.

In another aspect, the present invention leads to symptomatic and objective improvement in a cardiovascular disease condition, such as hypertension in man. By the term "symptomatic improvement," as used herein, reference is had to an improvement in a patient's subjective symptoms as reported by that patient. By the term "objective improvement," as used herein, reference is had to a measurable and objective change in the patient's condition (e.g. blood pressure), from an initial (at the start of treatment) to a subsequent (during or after treatment) condition.

Naturally, an active antihypertensive agent of this invention is used, if at all in a mammal, at a pharmaceutically effective dose rate, that is, at a dose rate which is below the level of toxicity or of production of undesired side effects. Because of biological complexities, the complete biological effects of the active agents of this invention are not now known.

Other and further aspects, objects, purposes, advantages, aims, utilities, features, and the like will be apparent to those skilled in the art from a reading of the present specification.

DETAILED DESCRIPTION

More particularly, this invention concerns a process for treating a human to control, ameliorate, or prevent a cardiovascular disease such as hypertension wherein there is introduced, preferably orally, into such a human a pharmaceutically effective amount of an active agent of this invention, preferably sodium bisulfite.

In one preferred mode of using this invention, an aqueous solution of from about 1 to 15% by weight sodium bisulfite is prepared. Then such solution is orally consumed by a human, for example, in the form of drops, at a total (or accumulated) dose rate ranging from 0.2 to 20 mg per each kilogram of body weight per day, more preferably in the form of from two to four spaced doses per day, each such dose being preferably taken around meal time.

Symptomatic and/or objective improvement in a patient's hypertensive condition even at relatively low dosage rates may occur within two weeks to four months of such a continuous oral usage of sodium bisulfite in accord with these teachings of this invention.

Such dilute sodium bisulfite solutions can be used before, during, or after the onset of a cardiovascular disease with beneficial results. Even when used on patients who might be considered terminally affected by such condition, beneficial results are observable.

It is believed that larger and/or smaller such doses can be used without departing from the spirit and scope of the present discovery. One dose rate, for example, which has usually been found to effective for man varies from about 0.2 to 75 mgm per day per average human adult patient (e.g. about 70 kg) of sodium bisulfite taken orally as a dilute aqueous solution of from about 1 to 5 percent by weight in distilled water and ingested before, during or after each of the daily meals, such as breakfast, lunch, and dinner. Presently, a preferred dose rate for a patient using a self-administered dilute aqueous system comprises one in the range from about 1.0 to 20 mgm per kg of body weight per day taken in the form of at least two spaced oral doses (using such an aqueous solution as described herein).

Because of a tendency for inorganic bisulfite and sulfites to undergo oxidation when in aqueous solution when oxygen is present, it is presently common and even preferred in using this invention to employ a solution which comprises on a 100 percent by weight total solution basis:

(a) from about 1 to 15 percent by weight of dissolved inorganic solids, and (b) the balance up to 100 percent by weight of any given solution being water.

In such solution, such dissolved inorganic solids comprise on a calculated 100 percent by weight dry basis:

(a) at least about 50 and more preferably at least about 90 percent by weight of inorganic bisulfite or sulfites salts, and (b) the balance up to 100 percent by weight thereof being inorganic compounds produced or producible by the oxidation of said inorganic salts.

The water used in such a solution is preferably purified (e.g. filtered, deionized, distilled or the like). After preparation, such a solution is preferably stored in a closed container to reduce oxidation.

Such an aqueous solution can be directly consumed by a patient as drops (e.g. from about 5 to 20 drops per meal, depending upon dose rate for an individual patient), or as a capsule, or the like, as desired.

A subjective improvement in atherosclerosis has been reported by some patients who have been dosed as described above with sodium bisulfite solutions. It may be that use of this invention exerts a favorable influence on blood lipids, such as a fall in total cholesterol.

One important advantage of the present invention is the circumstance that the indicated desirable results are achieved with little or no apparent side effects surprisingly. For example no change in a normal excretion rate of such metallic ions as sodium, potassium, magnesium, or calcium through urine appears to be associated with the use of active agents of this invention, contrary to normal experience with conventional diuretic agents which are used to lower blood pressure.

The active agents of this invention can be administered by any convenient or appropriate procedure. For example, injection by intravenous, intraperitoneal, intramuscular or subcutaneous administration of such a dilute aqueous solution as described above may afford a more rapid reduction in blood pressure than is observable from oral administration for reasons which are not presently known. Suppositories containing active agents can be used for absorption.

The active agents of the present invention can be formulated in any desired manner for administration. For example, conventional excipients, extenders, compounding agents and the like can be blended with powdered active agents and the resulting blends can be tableted, pilled, pelletized, or the like and then used as solid dosage forms. Conveniently, individual dosage units, in whatever form prepared or compounded, can range from about 50 to 500 milligrams (mg) each.

Per diem (24 hour day) dose rates for active agents of this invention for mammals (including man) are believed to range from about 0.2 to 50 mg per kg of body weight, with doses ranging from about 1 to 20 mg per kg being more general, convenient and typical for practical, safe administration. Larger and smaller dose rates can be employed without departing from the spirit and scope of this invention.

Embodiments

The present invention is further illustrated by reference to the following case histories. Those skilled in the art will appreciate that other and further embodiments are obvious and within the spirit and scope of this invention from the teachings of these present examples taken with the accompanying specification.

Preparation of Solutions

A

A solution of sodium bisulfite is prepared by dissolving pharmaceutical grade (U.S.P. Grade) powdered sodium bisulfite (sodium metabisulfite) in distilled water at room temperature to form a 1 percent by weight aqueous solution.

This solution is then placed into a series of plastic squeeze bottles, each with a volumetric capacity of about 50–52 ml. Each bottle is provided with a cap permitting drop-wise dispensing of solution from such bottle at an estimated rate of 15 drops per ml.

B

A solution of sodium bisulfite is prepared by dissolving pharmaceutical grade (U.S.P. Grade) powdered sodium bisulfite (sodium metabisulfite) in distilled water at room temperature to form a 2 percent by weight aqueous solution.

This solution is then placed into a series of squeeze bottles, each with a volumetric capacity of about 50–52 ml. Each bottle is provided with a cap permitting drop-wise dispensing of solution from such bottle at an estimated rate of 15 drops per ml.

C

A solution of sodium bisulfite is prepared by dissolving pharmaceutical grade (U.S.P. Grade) powdered sodium bisulfite (sodium metabisulfite) in distilled water at room temperature to form a 2.5 percent by weight aqueous solution.

This solution is then placed into a series of plastic squeeze bottles, each with a volumetric capacity of about 50–52 ml. Each bottle is provided with a cap permitting drop-wise dispensing of solution from such bottle at a rate estimated to be 15 drops per ml.

D

A solution of sodium bisulfite is prepared by dissolving pharmaceutical grade (U.S.P. Grade) powdered sodium bisulfite (sodium metabisulfite) in distilled water at room temperature to form a 5 percent by weight aqueous solution.

This solution is then placed into a series of plastic squeeze bottles, each with a volumetric capacity of about 50–52 ml. Each bottle is provided with a cap permitting drop-wise dispensing of solution from such bottle at an estimated rate of 15 drops per ml.

E

A solution of sodium bisulfite is prepared in distilled water to form a 10% by weight solution in distilled water. It is placed in a plastic squeeze bottle as above.

F

A solution of potassium metabisulfite is prepared by dissolving potassium metabisulfite in water to form a 15% by weight solution. It is dispensed from a plastic squeeze bottle.

G

As in F a solution of ammonium sulfite in water is made by dissolving ammonium sulfite in water to form a 10% by weight solution. It is dispensed from a plastic squeeze bottle.

In each of the following numbered case histories (1–24) each patient is provided with such a bottle of solution D, unless otherwise noted, and is instructed to dose himself (or herself, as the case may be) from the bottle so provided at the rate of seven drops to be taken orally with each of his (her three daily meals. When the contents of one such bottle is thus so gradually consumed by an individual patient, another is provided to him (her).

EXAMPLE 1

A 67 year old man, height 5'6" weight 56.8 kilograms, apparently had generalized poor arterial circulation. He would get cramps in his legs when he stood up for more than half an hour or walked a short distance, and the tips of his fingers had a cyanotic color, especially on cold days. It was felt that he suffered from generalized atherosclerosis. He had also sustained a heart attack about 3 years previously, and was afflicted by a cardiac arrhythmia and hypertension.

After about one month of this continuous dosage with Solution D, this man had improved. No recurrence of his original condition including hypertension was observed after about three years of continuously following this dosage.

EXAMPLE 2

A woman, age 50, height 5'5", weight 53.6 kilograms, had a high level of urea in the blood due apparently to nephrosclerosis. It was felt that she also had hypertension and generalized atherosclerosis.

After about two weeks of treatment with Solution D, she began to experience a remarkable improvement and her blood urea nitrogen level fell to normal. No recurrence of her original symptoms was observed after almost three years of continuous use of this substance.

EXAMPLE 3

A man, age 66, height 5'6", weight 71.8 kilograms, had a severe arterial insufficiency of such degree that one of his toes was to be amputated because of impending gangrene. It was felt that he had atherosclerosis. He also had coronary deficiency and hypertension. He was unable to sleep because of night pain in the foot.

After about 2 weeks of continuous treatment with Solution D, he was sleeping well. Also, the black area on his toe had disappeared. No recurrence of his original symptoms or signs were observed after about $4\frac{1}{2}$ years of continuous use of this solution.

EXAMPLE 4

A woman, age 48, height 5'4", weight 61.3 kilograms, complained of intermittent attacks of intense constricting pain in the chest felt to be angina pectoris due to coronary atherosclerosis and hypertension.

After about two weeks of continuous treatment with Solution D, she began to show a substantial relief from the pain in her chest. Continuance of the treatment resulted in a loss of all her symptoms in about 2 months, and, for about $2\frac{1}{2}$ years there has been no recurrence of her original symptoms.

EXAMPLE 5

A man, age 32, height 5'10", weight 81.8 kilograms, had a myocardial infarction at the age of 29, and he had been treated with heparin as an anticoagulant and also with vasodilator agents. It was felt that he had coronary atherosclerosis and hypertension. He was also on a special low salt, low fat diet.

This man improved symptomatically (in the patient's estimation) after about 2 weeks of treatment with Solution D. A gradual lowering of his heparin dose was achieved, and also of his vasodilator medicines. With continuance of the treatment, this man has been enjoying good health for about 3 years.

EXAMPLE 6

A woman, age 63, height 5'5", weight 86.3 kilograms, had a long history of severe varicose veins in her legs, and the right leg had become so swollen that she could scarcely walk.

After about 1 month of treatment with Solution D, her swollen leg returned to normal, and her varicose condition improved as demonstrated by reduced size of the varices. After about 4 years of continuous use of Solution D, no recurrence of her original condition has resulted.

EXAMPLE 7

A man, age 65, height 5'11", weight 77.3 kilograms, had suffered from constipation for many years and had developed hemorrhoids which bled frequently.

After taking Solution D for about 2 weeks, he began to experience normal bowel movements. His hemorrhoids subsquently became reduced in size. After about 3 years of continued use of Solution D, his bowels function normally. His hemorrhoids have stopped bleeding.

EXAMPLE 8

A man, age 72 at death, height 6', weight 86.4 kilograms, suffered an injury to his leg complicated by an embolus, which apparently had its inception in the leg, moved to the brain, and paralyzed the right side of his body. Subsequently he began to have thrombophlebitis in both his legs.

After use of Solution D was started, his phlebitis gradually disappeared. Beneficial results began to be observed in about two weeks. His paralysis did not regress; he continued to be bed ridden. After almost two years of continuously using Solution D, he had not experienced any return of phlebitis to his legs. However this man died from kidney infection.

EXAMPLE 9

A man, age 77, height 5'8", weight 79.5 kilograms, had severe hypertension for about 20 years which apparently caused him to have seven hemorrhages in his right eye, on successively different occasions. He had tried many antihypertensive medications to no avail. He had been on very strict, low salt and low fat diets.

After about two weeks of using Solution D, his blood pressure started to return to normal. After about 4 years of continuous use, his blood pressure has remained normal and no further hmorrhages have been experienced.

EXAMPLE 10

A man, age 67, height 5'10", weight 77.3 kilograms, had severe high blood pressure. He could no longer work, and was quite resigned to die.

After about two weeks of use of Solution D, his mental outlook had improved. Blood pressure gradually returned to normal. Later, the man returned to work and married. After about 4 years of continuous treatment with Solution D, his condition has not deteriorated.

EXAMPLE 11

A man, age 45, height 5'10", weight 70.5 kilograms, had labile high blood pressure for 25 years. When his blood pressure was at its highest point, he had epistaxis. His doctor recommended cauterization of his nose veins to avoid bleeding at night when he was sleeping. Many antihypertension medications were tried with no observed beneficial results.

After commencing treatment with Solution D, he experienced a stabilized and normalized blood pressure apparently within about three weeks. Good health has now been enjoyed for about 2½ years.

EXAMPLE 12

A man, age 77 at death, height 5'9", weight 77.3 kilograms, had gradually deteriorating health. It was felt that he had hypertension atherosclerosis and visceral congestion and also that he had increasing pulmonary insufficiency apparently due to tobacco use. His whole body was swollen and his physicians were treating him with steroids. He was considered to be terminal.

Within two weeks after starting Solution D, his general condition improved. After about three years of continuous use of Solution D, this man continued to be well, except for his pulmonary emphysema which did not improve. He is now deceased.

EXAMPLE 13

A man, age 62, height 5'9", weight 86.4 kilograms, had had a previous heart attack. He was found by his physician to have high levels of sugar in his blood and urine. It was felt that he had hypertension, diabetes, and atherosclerosis. His physician prescribed an oral medicine to help stabilize his blood sugar. Subsequently, he suffered a second heart attack, and then a third. His condition was critical when solution D was started.

After about 1 and ½ months of consuming the solution, his condition improved. After about 3 years of continuous use of the solution, he has experienced no further heart attacks and his blood sugar levels have decreased. He is ambulatory with restrictions, and his hypertension is controlled.

EXAMPLE 14

A man, age 78, height 5'11", weight 82 kilograms, had mild hypertension, mild arthritis, mild arrhythmia, hemorrhoids, dispepsia, cyanotic fingers and toes, mild diabetes, general malaise, and lassitude. After his gall bladder had been removed at age 66, his digestion deteriorated. His diabetes was acquired shortly before treatment with sodium bisulfite began and has been controlled continuously since with diabinese (500 mg daily).

After oral ingestion of aqueous solutions of sodium bisulfite of various concentrations (Solutions A, B, C and D) at dose rates varying from 4 to 20 drops per meal, all of the above identified conditions improved (except for diabetes) within 2-3 months. Thereafter, they gradually disappeared and never recurred. After about seven years of continuous experimental use, the man remains in good health, and is alert and vigorous with excellent color.

After about 3-4 years of use, the man found that he had a prolonged blood clotting time whereupon he reduced his dosage rate somewhat to about 8 drops per meal per day of solution D and his blood clotting time then normalized.

Samples of about 4 cc each of his blood were prepared. To each of these was added about 10 drops of a solution of 10 weight percent sodium bisulfite in distilled water. Each sample was then sealed into a glass vial. After about 2½ years storage at ambient temperatures, these blood sample have not coagulated.

EXAMPLE 15

A widowed woman, age 54, height about 5'5", weight about 60 kilograms, had hypertension, backaches, headaches, and some nervousness. Her blood pressure was 160/110.

After oral consumption of solution D at the rate believed to be about 6 drops per each of three daily meals for about 10 days to 2 weeks, her hypertension began to diminish and after about two months of usage reportedly stabilized at about 120/90. Her backaches, headaches, and depression all disappeared. Use of solution D continues.

EXAMPLE 16

A woman, age 62, height about 5'7", weight about 62 kilograms had hypertension for 10 years with symptoms which included shortness of breath especially when walking, getting red in the face, headaches, dizzyness, and inability to exercise. Her blood pressure was 190/130.

After oral consumption of solution D at the rate believed to be about 6 drops per each of three daily meals, her blood pressure was reduced to 160/90. Between the second and third months of use of solution D, all above symptoms went away. Use of solution D continues.

EXAMPLE 17

A woman, age 86 years, had hypertension. Her blood pressure was 200/120.

After use of Solution D at the dose rate believed to be about 6 drops per each of three daily meals, her blood pressure fell to a value in the range from about 160-170 to 90-100 and is being maintained at these reduced values through continued use of solution D.

EXAMPLE 18

A woman, age about 45 years, had hypertension. Her blood pressure was 190/110.

After use of solution D at a dose rate believed to be about 7 drops per each of three daily meals, her blood pressure fell to about 150/90 within about 10 days. Thereafter, use of agent D was discontinued.

EXAMPLE 19

A hypertensive human, about 60 years of age had a blood pressure of about 170/110.

After 7 to 8 days of oral consumption of solution D at the rate believed to be about 7 drops per each of three daily meals, the patients blood pressure was reduced to 160/90. On the 10th day, a slight rise in blood pressure was observed. Use of solution D was then discontinued.

EXAMPLE 20

A woman, about 68 years old, had had hypertension all her life. She was strongly claustrophobic. Also, she had varicose veins. Her blood pressure was 170/100.

After use of solution D for 6 months at the rate believed to be about 14 to 21 drops per day (about seven drops for each of her daily meals), her blood pressure was reduced to 136/86. Use of solution D continues.

EXAMPLE 21

A man, age 44, weight 82 kilograms, had hypertension. His blood pressure was 170/120, sometimes 160/110.

After consumption of solution D for about 3 months at the rate of about 7 drops per meal per day (man eats 2 meals per day) for about 3 months, his blood pressure dropped from about 140/110 to 140/90. The man, by opthalmological exmination, was found to have grade 2 eye grounds.

The man at one point discontinued use of solution D. Within two weeks his blood pressure increased. He started using solution D again at the same dose rate and his blood pressure again was reduced to the values above given.

EXAMPLE 22

A man, age 70 weight 64 kilograms, had had hypertension for four years. Three years ago he had had a neck hematoma (in back of one ear) and an embolus in the brain. He experienced no physical residuals but can now speak only slowly and has poor sensibility in his fingers (three have no sensitivity to tough). His blood pressure was 195/100.

After about one year of using solution D at the rate of 6 to 7 drops per each of 3 daily meals, his blood pressure was reduced to about 145/90. Use of solution D continues.

EXAMPLE 23

A man, age 43, weight 74 kilograms, had had hypertension for 15 years. His blood pressure rose occasionally to 180/110.

After about two and one half years of using solution D first at the rate of 15 drops per day and now at the rate of about 14 drops per day for 6 months, his blood pressure was found to be about 170/100 and at times is 140/87. Opthalmoscopic exmination reveals normal eyes. Use of solution D continues.

EXAMPLE 24

A man, age 47 weight 93 kilograms had hypertension and a blood pressure of 160/100.

After using solution D for about 2 months at the rate of about 10 drops per each of 3 daily meals, his blood pressure was 125/85.

After a further period of use, the man discontinued use of solution D. Within 9 days, his ears began to buzz and his blood pressure went up in about 8 days. He started use of solution D again at the same dosage rate and his blood pressure again dropped. Currently, his blood pressure was found to be about 140/106. Use of solution D continues.

EXAMPLE 25

Under the supervision of a physician, a series of 8 patients, who are found to be hypertensive initially are each provided with a material termed "Agent C" which is actually a solution in water of sodium bisulfite supplied in plastic squeezed bottles which are each adapted for drop-wise dispensing of the solution charge thereinto. The solution, at a measured drop dosage, is administered orally to the patient by himself at each one of his daily meals. Any other treatment received by the patient was suspended when the treatment began. Periodic observations by the doctor of each patient were carried out. Besides hypertenive symptoms, other symptoms should indicate secondary effects of an undesirable or adverse nature, such as nausea, vomiting, dizziness, fainting, irritability, blurred vision, etc. were investigated. No adverse secondary effects were observed.

Case 1

| Male | |
|---|---|
| Age | 64 |
| Occupation | Accountant |
| Weight | 73 kg |
| Starting Blood Pressure | 150/120 |
| Dose: 7 drops 3 times a day | |
| Readings: | |
| January 6, year one | 150/120 |
| March 8, year one | 145/115 |
| June 6, year one | 140/115 |
| Sept. 20, year one | 130/95 |
| January 6, year two | 130/85 |
| April 2, year two | 130/80 |

Case 2

| Male | |
|---|---|
| Age | 37 |
| Occupation | Grocer |
| Weight | 75 kg |
| Starting Blood Pressure | 140/98 |
| Dose: 8 drops 3 times a day | |
| Readings: | |
| December 15, year one | 140/98 |
| April 24, year two | 130/80 |
| May 4, year two | 130/80 |

Case 3

| Male | |
|---|---|
| Age | 65 |
| Weight | 72 kg |
| Starting Blood Pressure | 180/135 |

Note: For 3 years previously, this patient was treated for hypertension using such products as Aldomet and Hygraton with reserpine.

| | |
|---|---|
| Dose: 8 drops 3 times a day | |
| Readings: | |
| September 7, year one | 180/135 |
| October 11, year one | 170/135 |
| December 20, year one | 170/135 |
| January 25, year two | 165/130 |
| May 9, year two | 160/90 |
| October 12, year two | 150/90 |
| February 21, year three | 130/85 |
| July 5, year three | 135/85 |
| December 13, year three | 135/80 |
| April 21, year four | 135/75 |

Case 4

| Male | |
|---|---|
| Age | 48 |
| Occupation | University Teacher |
| Weight | 63 kg |
| Starting Blood Pressure | 170/110 |
| Dose: 7 drops 3 times a day | |
| Readings: | |
| January 3, year one | 170/110 |
| February 24, year one | 160/110 |
| April 22, year one | 150/110 |
| June 20, year one | 145/100 |
| October 15, year one | 135/95 |
| January 15, year one | 135/90 |
| March 22, year two | 130/90 |
| May 12, year two | 130/85 |

Case 5

| Male | |
|---|---|
| Age | 43 |
| Occupation | Salesman |
| Starting Blood Pressure | 130/95 |
| Weight | 68 kg |
| Dose: 7 drops 3 times a day | |
| Readings: | |
| October 15, year one | 130/95 |
| January 13, year two | 130/90 |
| March 5, year two | 130/90 |
| May 12, year two | 130/70 |

Case 6

| Female | |
|---|---|
| Age | 42 |
| Occupation | housewife |
| Starting Blood Pressure | 150/95 |

-continued

Dose: 6 drops 3 times a day
Readings:
| | |
|---|---|
| November 9, year one | 150/95 |
| January 6, year two | 150/98 |
| May 15, year two | 135/90 |
| September 20, year two | 130/80 |
| December 14, year two | 130/70 |
| March 13, year three | 130/70 |
| May 12, year three | 130/70 |

Case 7

| | |
|---|---|
| Male | |
| Age | 54 |
| Occupation | Civil Engineer |
| Weight | 75 kg |
| Starting Blood Pressure | 140/110 |
| Dose: 6 drops 3 times a day | |
| March 14, year one | 140/110 |
| June 21, year one | 140/110 |
| September 27, year one | 135/100 |
| December 14, year one | 135/95 |
| February 12, year two | 135/90 |
| April 15, year two | 135/90 |
| May 18, year two | 130/85 |

Case 8

| | |
|---|---|
| Female | |
| Age | 27 |
| Occupation | Civil Engineer |
| Blood Pressure | 150/110 |
| Dose: 6 drops 3 times a day | |
| Readings: | |
| October 15, year one | 150/110 |
| December 27, year one | 150/105 |
| February 25, year two | 140/90 |
| May 14, year two | 140/90 |

EXAMPLE 26

A series of 4 patients are examined. Each one maintains that he was previously hypertensive and each one maintains that he has been regularly orally ingesting a liquid material known to him only as "Agent C" which is in fact a 10.3 weight percent solution in water of sodium bisulfite. Treatment with other medications ceased. Each one is examined by a physician to determine his current blood pressure. Each case is reported below:

Case 1:
  Male, age 74. Occupation: Lawyer.
  Starting blood pressure: 160/100
  Current blood pressure: 140/90
Case 2:
  Male, age 61. Occupation: Engineer.
  Starting blood pressure: 160/80
  Current blood pressure: 140/70
Case 3:
  Male, age 72. Occupation: Doctor-surgeon.
  Starting blood pressure: 170/105
  Current blood pressure: 130/65
Case 4:
  Female, age 58. Occupation: Housewife.
  Starting blood pressure: 180/130
  Current blood pressure: 140/80

EXAMPLE 27

To demonstrate the effectiveness of agents of the present invention experiments were carried out on hypertensive rats.

Rats of the SHR (spontaneous hypertensive rat) strain weighed about 250 g, were anesthetized with urethane (ethyl carbamate) using 1500 milligrams per kilogram IP. The trachea is cannulated to avoid respiratory distress and the body temperature maintained constant with a heated pad controlled from a rectal sensor. The carotid artery was cannulated with a fine nylon catheter connected to a Honeywell blood pressure transducer filled with heparinized saline. The mean and phasic blood pressures were recorded on a Device F19 multi-channel recorder. Test substances were administered by the intra-peritoneal route, unless otherwise stated. Soluble materials were given as aqueous solutions and insoluble materials as emulsions or suspensions in aqueous vehicles. The test substances were given at a series of increasing dose levels each subsequent dose being twice the previous dose. The results quoted in the Table give the lowest dose level firstly to cause a clear lowering of blood pressure and secondly the dose found to cause the death by the preparation.

TABLE 1

Hypertensive and Toxic Dose Levels of Sulfite Derivatives

| Substance | Route of Administration | Hypertensive Dose Level mg/kg | Toxic Dose Level mg/kg |
|---|---|---|---|
| Sodium Bisulfite | IP | 100 | 1000 |
| Potassium Bisulfite | IP | 117 | 467 |
| Calcium Bisulfite | orally | 1016 | not obtained |
| Ammonium Bisulfite | IP | 104 | 1664 |
| Magnesium Bisulfite | IP | 176 | 1408 |

Clearly agents of the present invention are capable of lowering blood pressure in test animals.

I claim:

1. A method of treating hypertension in a human suffering from said condition comprising introducing into said human an antihypertensively effective amount of a compound selected from the group consisting of alkali metal, alkaline earth metals and ammonium sulfites and bisulfites, and alkali metal metabisulfites at a pharmaceutically effective rate of from about 0.2 to 50.0 mgm thereof per kilogram of body weight per 24 hours.

2. The method of claim 1 in which the antihypertensive compound is sodium bisulfite.

3. The method of claim 1 in which the antihypertensive compound is sodium metabisulfite.

4. The method of claim 1 in which said compound is administered orally.

* * * * *